(12) United States Patent
Riddles

(10) Patent No.: US 6,718,914 B2
(45) Date of Patent: Apr. 13, 2004

(54) METHOD FOR NEUTRALIZING OFFENSIVE CHEMICAL ODORS

(76) Inventor: Philip J. Riddles, 1 Whitney Dr., New Fairfield, CT (US) 06812

( * ) Notice: Subject to any disclaimer, the term of this patent is extended or adjusted under 35 U.S.C. 154(b) by 0 days.

(21) Appl. No.: 10/201,496

(22) Filed: Jul. 23, 2002

(65) Prior Publication Data

US 2004/0016410 A1 Jan. 29, 2004

(51) Int. Cl.⁷ .............................. A61K 7/50; A61L 9/01
(52) U.S. Cl. ................... 119/651; 119/603; 424/76.1
(58) Field of Search ................. 119/603, 651, 119/650, 601; 424/76.1, 76.2, 76.21, 76.4, 76.6; 208/310

(56) References Cited

U.S. PATENT DOCUMENTS

| | | | |
|---|---|---|---|
| 4,078,050 A | * 3/1978 | Hart | 424/76.1 |
| 4,202,882 A | 5/1980 | Schwartz | 424/76.2 |
| 4,594,239 A | * 6/1986 | Pluim, Jr. | 424/10.3 |
| 4,803,047 A | 2/1989 | Pluim, Jr. | 422/5 |
| 4,805,520 A | * 2/1989 | Freedman | 454/157 |
| 4,806,274 A | * 2/1989 | Crouse et al. | 510/104 |
| 4,834,901 A | 5/1989 | Wiesner | 510/109 |
| 4,867,045 A | * 9/1989 | Freedman | 454/157 |
| 5,254,337 A | * 10/1993 | Marcus et al. | 424/76.1 |
| 5,462,688 A | 10/1995 | Lippman et al. | 510/139 |
| 5,523,014 A | 6/1996 | Dolan et al. | 510/396 |
| 5,976,549 A | * 11/1999 | Lewandowski | 424/754 |
| 6,177,070 B1 | 1/2001 | Lynch | 424/76.1 |

OTHER PUBLICATIONS

"Chemical Composition Of Striped, Spotted, And Hog-Nosed Skunk Musk", http://granicus.if.org/~firmiss/m–d/skunk–chem.html.

"Beyond Tomato Juice: Skunk Spray Remedies", http://granicus.if.org/%7Efirmiss/m–d/skunk–remedies.html.

"Deskunking Dogs, Cats, and Other Pets", http://dan.drydog.com/patsyann/skunk.html.

* cited by examiner

Primary Examiner—Yvonne Abbott

(57) ABSTRACT

A method is provided for neutralizing the odor of low molecular weight thiols, such as found in skunk spray, in an affected area. An effective amount of a cleaning composition including an oil phase having at least one of a hydrocarbon oil and a hydrocarbon solvent, and a water phase containing water and a base is applied to the affected area. The affected area is shampooed with the cleaning composition thereby neutralizing the offensive odor.

5 Claims, No Drawings

METHOD FOR NEUTRALIZING OFFENSIVE CHEMICAL ODORS

BACKGROUND OF THE INVENTION

The present invention relates to methods and techniques for neutralizing the odiferous smell of offensive chemicals. More particularly, this invention relates to neutralizing the odor of low molecular weight thiols.

Exposure to skunk spray is a great annoyance because of its very disagreeable and persistent odor due to low molecular weight thiols. The odor may persist for several days on anything contacted by the spray, e.g., wearing apparel, pets, personal articles, and the like. In particular, dogs are often exposed to the spray and become a nuisance when attempts are made to decontaminate them.

Because the skunk spray is hydrophobic, removal of the spray and the primary odor-causing factors (n-butanethiol and 2-methylbutanethiol) by ordinary means such as soap and water is very difficult. Soaking exposed articles in tomato juice or perfumed detergents for extended periods has been suggested but has not proven particularly effective.

It has also been suggested that thiols can be deodorized by use of a hydrogen peroxide/baking soda combination. However, this creates a harsh solution and must be kept away from an animal's eyes. Further, hydrogen peroxide and baking soda, when placed in a closed container, can be a hazardous and explosive combination.

SUMMARY OF THE INVENTION

In accordance with the present invention, methods and techniques are described for effectively neutralizing the odor of low molecular weight thiols such as are present in skunk spray. Thus, the invention is effective for eliminating the offensive odor of skunk spray and similar offensive chemicals from wearing apparel, pets, personal articles, and other affected objects.

More particularly, a method is disclosed for neutralizing the odor of low molecular weight which includes the application to the affected area an effective amount of a cleaning composition. The cleaning composition has an oil phase including at least one of a hydrocarbon oil and a hydrocarbon solvent and mixtures thereof, and a water phase containing water and a base. The affected area of the object is thoroughly shampooed with the cleaning composition thereby neutralizing the disagreeable odor of the offensive chemical.

DETAILED DESCRIPTION OF THE INVENTION

The invention herein is directed toward the application of a cleaning composition, typically in the form of an emulsion or an emulsion gel, for neutralizing the odiferous smell of offensive chemicals.

The cleaning composition used in the present invention preferably includes an oil phase and a water phase, the oil phase containing at least one of a hydrocarbon oil and a hydrocarbon solvent, and at least one of a fatty acid and a surfactant, and the water phase containing water and some sort of alkali or amine base. However, it will be understood that each ingredient is not necessarily required to be added as a part of a phase, that is, the ingredients can be added independently of one another regardless of the phase. Nevertheless, for ease of discussion, the different components are discussed with regard to the oil and water phases.

It will be appreciated that numerous other components such as fragrances, dyes, colorants, pigments, preservatives, emollients, and thickeners can also be utilized in the cleaning composition.

The hydrocarbon oils and solvents used in the oil phase of the cleaning composition are well known in the art. The hydrocarbon oil component is an oil which generally cuts and dissolves viscous organic materials such as grease, sludge and the like. Generally, any non-drying and non-irritating organic mineral oil can be utilized and includes, by way of example, petroleum mineral oils such as aliphatic and wax-based oils, aromatic or asphalt-based oils, or mixed-based oils. One desirable oil is white mineral oil such as is readily available from a large number of manufacturers. Other hydrocarbon oils are well known in the art and in the literature. Additionally, all or a portion of the hydrocarbon oil can be extended with conventional or common solvents complementary to or compatible with the hydrocarbon oils. One such suitable solvent commonly used is odorless mineral spirits.

Generally, the hydrocarbon oil and solvent comprise from about 25 to about 60 percent by weight of the total cleaning composition which can, in turn, comprise all mixtures of oil and solvent from 0 to 100 parts by weight of each to total 100 parts of hydrocarbon oil/solvent. Desirably, the oil and solvent includes from about 30 to about 55 percent by weight and preferably from about 40 to about 55 percent by weight of the total cleaning composition.

The fatty acid in the oil phase of the cleaning composition may include a variety of oils and fats having from about 6 to about 20 carbon atoms. Typical commercial blends such as oleic fatty acid, coconut fatty acid, soya fatty acid and tall oil fatty acid can be utilized. Preferably, the fatty acid comprises from about 5 to about 10 percent by weight of the total cleaning composition.

The fatty acid or a fatty acid ester is commonly used in conjunction with an alkali or base from the water phase to form a soap, that is, the salt of a fatty acid. Inorganic alkalis such as potassium hydroxide, sodium hydroxide, ammonium hydroxide, soda ash and ammonia may be used. In addition, one or more non-fatty acid soap surfactants can be included in the oil phase of the cleaning composition in amounts preferably ranging from about 2 to about 10 percent by weight. Numerous surfactants can be utilized and are well known in the art.

An optional component of the cleaning composition generally found in the oil phase is a solubilizer such as propylene glycol, sorbitol, glycerin, and the like. Solubilizers are utilized to help maintain various additives, in solution which otherwise are not generally soluble in water, as for example various fragrances, preservatives and the like. They also impart mildness to the cleaning composition and impart good freeze-thaw properties. Examples of other suitable solubilizers are known in the art as well as the literature. The amount of such solubilizers generally ranges from about 1 to about 5 percent by weight and desirably from about 1 to about 3 percent by weight.

In the water phase, water is used to form an emulsion with the amount varying based upon the type of cleaning composition desired, e.g., an emulsion, an emulsion gel, etc. Typically, the amount utilized is from about 30 to about 55 percent by weight, with about 30 to about 46 percent by weight being preferred.

As discussed above, the water phase may also include a base such as an amine or a hydroxide. Where such a base is employed, it is preferred that from about 0.2 to about 5 percent by weight be employed. The base is utilized in conjunction with the fatty acid to produce a soap on an equivalent basis of from about 2.7 to 0.8 equivalents to 1 equivalent of base. Examples of suitable base inorganic alkalis, such as potassium hydroxide, sodium hydroxide, ammonium hydroxide and ammonia.

Finally, various other common and conventional additives can be utilized in suitable or conventional amounts. Examples of such additives include preservatives, colorants, dyes, pigments, fragrances, emollients, thickeners, and the like, the total amount of such additives is generally small and typically within the range of from about 0.5 to about 3 percent by weight when present, with from about 1 to about 2 percent by weight being preferred for additives.

In accordance with the invention, the cleaning composition is applied to the affected area, for example, the area of an object sprayed by a skunk. The area is thoroughly shampooed with the cleaning composition and then either rinsed or wiped clean. The affected area is thereby neutralized of the disagreeable odor of the offensive chemical.

EXAMPLE

A suitable cleaning composition for the removal of the persistent odor due to low molecular weight thiols is as follows:

Mineral Spirits
Water (Aqua)
Mineral Oil (Parafin Liquidum)
Tall Oil Acid
Nonoxynol-9
Sodium Hydroxide
Propylene Glycol
Petrolatum
Nonoxynol-6
Ethanolamine
Lanolin
Zinc Pyrithione This cleaning composition is marketed by GOJO industries, Inc. (Cuyahoga Falls, Ohio) as "Original Formula Hand Cleaner". The cleaning composition was applied to a dog that had an unfortunate encounter with a skunk. The dog was wet down with water from a garden hose, the cleaning composition was applied and thoroughly lathered into the fur, and then the dog was rinsed and dried. One application of the cleaning composition almost completely neutralized the odor to the point where the odor was not noticeable when in a closed room with the animal.

While the invention has been described in its preferred embodiments, it is to be understood that the words which have been used are words of description, rather than limitation, and that changes may be made within the purview of the appended claims without departing from the true scope and spirit of the invention in its broader aspects.

What is claimed:

1. A method of neutralizing the odor of low molecular weight thiols in animal fur, comprising the steps of:

applying to the fur an effective amount of a cleaning composition including an oil phase having at least one of a hydrocarbon oil and a hydrocarbon solvent, and a water phase containing water and a base; and shampooing the fur with said cleaning composition.

2. The method according to claim 1, further comprising the step of including at least one of a fatty acid and a non-fatty acid soap surfactant in said cleaning composition.

3. The method according to claim 2, further comprising the step of including a solubilizer in said cleaning composition.

4. The method according to claim 3, further comprising the step of applying said cleaning composition to the fur of a dog.

5. The method according to claim 1, further comprising the step of applying said cleaning composition to the fur of a dog.

\* \* \* \* \*